United States Patent

Döring et al.

Patent Number: 5,968,837
Date of Patent: Oct. 19, 1999

[54] PHOTO-IONIZATION ION MOBILITY SPECTROMETRY

[75] Inventors: Hans-Rüdiger Döring; Gerd Arnold; Joachim Adler; Thomas Röbel; Jürgen Riemenschneider, all of Leipzig, Germany

[73] Assignee: Bruker-Saxonia Analytik GmbH, Leipzig, Germany

[21] Appl. No.: 08/815,421

[22] Filed: Mar. 11, 1997

[30]     Foreign Application Priority Data

Mar. 12, 1996 [DE]    Germany .................. 196 09 582

[51] Int. Cl.⁶ ............... G01N 33/00; H01J 49/00; B01D 59/44
[52] U.S. Cl. .................. 436/173; 250/281; 250/282; 250/288; 436/139; 436/104; 436/111; 436/120
[58] Field of Search .................. 436/173, 139–142, 436/104, 111, 120; 250/281, 282, 288

[56]     References Cited

U.S. PATENT DOCUMENTS

| | | | |
|---|---|---|---|
| 3,621,239 | 11/1971 | Cohen | 250/41 |
| 4,317,995 | 3/1982 | Bradshaw et al. | 250/288 |
| 4,839,143 | 6/1989 | Vora et al. | |
| 4,928,033 | 5/1990 | Spangler et al. | |
| 5,032,721 | 7/1991 | Bacon et al. | 250/282 |
| 5,338,931 | 8/1994 | Spangler et al. | |

FOREIGN PATENT DOCUMENTS

| | | |
|---|---|---|
| 0135747 | 4/1985 | European Pat. Off. . |
| WO9311554 | 6/1993 | WIPO . |

OTHER PUBLICATIONS

F.W. Karasek *Res./Develop.* 1972, 23, 63–66.
R.A. Keller *Am. Lab.* 1975, 35–36, 38, 40, &42–44.
S. C. Subba Rao et al. *Anal. Chem.* 1978, 50, 511–515.
S.H. Kim et al. *Anal. Chem.* 1978, 50, 1784–1788.
D.M. Lubman et al. *Anal. Chem.* 1983, 55, 867–873.
M.A. Baim et al. *Anal. Chem.* 1983, 55, 1761–1766.
D.M. Lubman *Anal. Chem.* 1984, 56, 1298–1302.
K. Matsumoto et al, *Org. Mass Spectrom.* 1985, 20, 777–780.
Proctor, C.J. et al *Anal. Chem.* 1984, 56, 1794–1797.
V.J. Vandiver et al, *Int. J. Mass Spectrom. Ion Processes* 1985, 66, 223–238.
G.A. Eiceman et al. *Int. J. Environ. Anal. Chem.* 1987, 28, 279–296.
C. Allgood et al, *Org. Mass Spectrom.* 1990, 25, 497–502.
C. Allgood et al. *Anal. Chem.* 1991, 63, 721–725.
S.E. Bell et al, *J. Am. Soc. Mass Spectrom.* 1994, 5, 177–185.
G. A. Eiceman et al. *Anal. Chim. Acta* 1995, 306, 21–33.
Q. Meng et al, *Int. J. Environ. Anal. Chem.* 1995, 61, 81–94.
Byron Carnahan et al., *Development and Applications of a Transverse Field Compensation Ion Mobility Spectrometer*, from the Fourth International Workshop on Ion Mobility Spectrometry, Proceedings of an International Speciality Workshop, Aug. 6th–9th, 1995.
Gary A. Eiceman et al., *Ion Mobility Spectrometry*, pp. 51–53, 1994.
G. A. Eiceman et al., *Charge Exchange in Binary of Polycyclic Aromatic Hydrocarbons Using Photonization–Ion Mobility Spectrometry*, Analytical Chemistry, vol. 58, No. 11, Sep. 1986.

(List continued on next page.)

*Primary Examiner*—Arlen Soderquist

[57]     ABSTRACT

In a method for photo-ionization ion mobility spectrometry, a reagent gas is added, in particular an aromatic compound, which has a large ionization cross section in the range of ionizing VUV radiation, but a low probability for the formation of protonated quasi-molecular ions. In this way, the detection of only weakly proton affine substances is also amplified or even made possible at all, and also the detection of electronegative substances in a negative operating mode is improved. Preferred reagent gases are benzene, toluene and xylene. FIG. 1

9 Claims, 6 Drawing Sheets

OTHER PUBLICATIONS

J.W. Leonhardt et al., *Determination of Benzene, Toluene, and Xylene by means of an Ion Mobility Spectrometer Device using Photoionization*, pp. 49–56, Oct. 16–19, 1994.

W.B. Tzeng et al., *Multiphoton Ionization of Acetone Glusters: Metastable Unimolecular Decomposition of Acetone Cluster Ions and the Influence of Solvation on Intracluster Ion–Molecule Reactions*, J. Am. Chem. Soc, vol. 111, No. 16, pp. 6035–6045, 1989.

Z. Luczynski et al., *Reactions of the Solvated Proton System $H^+$ . . .* , International Journal of Mass Spectrometry and Ion Physics, vol. 23, pp. 37–44, 1977.

PHOTO-IONIZATION ION MOBILITY SPECTROMETRY

BACKGROUND OF THE INVENTION

The invention concerns a method for the detection of gas traces in the air with the help of a photo-ionization ion mobility spectrometer, whereby a sample gas is directed into a photo-ionization chamber and the sample molecules present in the sample gas are ionized by the VUV radiation of a, lamp and whereby this ionization is amplified by adding a reagent gas.

A method of photo-ionization ion mobility spectrometry is known from U.S. Pat. No. 5,338,931.

Ion mobility spectrometers operate similarly to time-of-fright mass spectrometers, however not under a vacuum, but rather at atmospheric pressure.

Ion mobility spectrometers (IMS) are used, for example, to detect the presence of substance vapors in an environment, such as of pollutants in atmospheric air. The possibilities range from a simple alarm function at the presence of known pollutants, e.g. a chemical warfare agent, through the identification of an unknown substance, to the quantitative determination of concentration.

Typical ion mobility spectrometers have an ionization source, a reaction cell, a drift cell, e.g. in the shape of a tube, an entrance grid between the reaction and drift regions, and an ion detector. The spectrometers operate at atmospheric pressure, where the mean free path length of the gas molecules in the drift cell is small compared to its dimensions. Usually, a carrier gas, i.e. dry air, is introduced into the spectrometer together with the sample gas or vapor. The carrier gas containing the sample is fed via an inlet to the ionization source, which causes the carrier gas and sample molecules to be partially ionized. The ionization source usually consists of $^{241}$Am or $^{63}$Ni. Through collisions, the charge from the carrier gas molecules is transferred to the sample molecules, meaning that quasi-molecular ions form. There is generally an electrical potential gradient in the reaction region, so that the charged mixture is moved toward the injection grid. The latter is electrically charged and normally bars admission to the drift cell. Periodically, this potential is lowered, however, for a brief time, so that a sample ion pulse moves into the drift cell. Here, there is an approximately constant electrical drift field, i.e. a constant potential gradient which moves the ions along the axis of the cell to a detector electrode located at the end of the drift cell opposite to the end with the injection grid, collecting the charge from the ions. The arrival time of the ions relative to the pulsed opening of the injection grid is dependent upon the mobility of the ions detected. Light ions are more mobile than heavy ions and reach the detector earlier. This effect is exploited for characterization of the ions. The pulsed opening of the grid can be repeated periodically in measuring cycles in order to increase the signal-to-noise ratio by the addition of subsequently acquired ion mobility spectra, or to perform a quasi-continuous measurement.

The use of a radioactive ionization source as an emitter of α or β rays limits application to the detection of those pollutants which are strongly proton affine or electronegative (basically these are only chemical warfare agents and explosives) and their use represents a certain risk especially in the nonmilitary area.

For this reason, and to expand the range of analytical applications, various efforts were undertaken how to replace the radioactive ionization sources. In U.S. Pat. No. 4,839,143 and U.S. Pat. No. 4,928,033, the use of alkali-cation emitters as ionization sources in ion mobility spectrometers is described. With these sources, ionization of the sample molecules is only possible during the positive operating mode of the ion mobility spectrometers. In this way, many electronegative pollutants evade ionization. Furthermore, considerable electrical power (in excess of one Watt) is required to heat the alkali emitter to temperatures of 600°C.–800° C., rapidly consuming batteries in a small battery-operated instrument.

In the international patent application WO 93/11554 A1, a corona discharge ionization source for an ion mobility spectrometers is presented. But also with this type of ionization source, electronegative pollutants are not detectable, since nitrous gases resulting from the discharge are very strongly electronegative, thus making a charge transfer to the generally weaker electronegative pollutant molecules impossible.

The application of vacuum-UV light for pollutant ionization is known from photo-ionization detectors (PID) which are used as detectors for gas chromatography or non-selective manual instruments. The VUV light is either generated by lasers, by low or high pressure lamps filled with inert gas, by constant current lamps or by flash lamps. In the above cited U.S. Pat. No. 5,338,931, a flash lamp is suggested as particularly advantageous. Although irradiation with VUV light in principle allows for the ionization of a large number of pollutant molecules, ionization is restricted to those substances with an ionization potential which is less than the energy hv of the light, and which can, in addition, absorb the light. Thus for example the molecules of 1,1-dimethylhydrazine fuel can hardly be ionized in the ppm range with the light of a 10.6 eV lamp because of its low absorbency, despite its low ionization potential of 7.3 eV.

In conjunction with ion mobility spectrometers, it is known that the addition of a chemical reagent gas such as acetone or carbon tetrachloride to the carrier gas can improve the detection selectivity. The initially cited U.S. Pat. No. 5,338,931 also suggests such an addition in conjunction with photo-ionization, particularly acetone, thereby quoting two articles, i.e. Luczynski and Wincel Int. J. Mass. Spectrometry and Ion Physics, Vol. 23, pp. 37–44 (1977) and Tzeng et al. in J. Am. Soc., Vol. 111, pp. 6035–6040 (1989). It is inferred from these articles that the ionization process takes place via the formation of protonated monomers $H^+(CH_3)_2CO$ and dimers $H^+[(CH_3)_2CO]_2$.

It is indicated in U.S. Pat. No. 5,338,931 that the addition of acetone not only increases selectivity but also detection sensitivity. It is asserted that it is not necessary for the reagent substance to have an ionization energy which is lower than the photon energy, since excited reagent molecules could be formed which are ionized through subsequent reactions. An "effective" ionization potential is therefore important. Without any further explanations, and particularly without any example, it is mentioned that the addition of a reagent gas can improve the sensitivity of an ion mobility spectrometers in the positive and negative mode.

For acetone, the only reagent substance explicitly described in U.S. Pat. No. 5,338,931, the ionization of the target substance to be detected proceeds via the intermediate formation of protonated dimers of the acetone molecule. Charge transfer to the target molecule occurs via the proton and not through direct ionization. The effectiveness of the charge transfer therefore depends for the most part upon the proton affinities of the molecules involved, not upon their ionization potential. It is absolutely necessary for the progress of the reaction that the proton affinity of the target substance is greater than that of acetone. Detection of non-proton affine target substances, such as of some hydrocarbons and chlorinated thioether, is therefore not amplified by the addition of acetone.

However, there is still a need for a method of operation for an ion mobility spectrometer with a VUV lamp as a non-radioactive ionization source for the detection of a target substance in air, in which selectivity and detection sensitivity are improved by the addition of a reagent gas which is also successful for less proton affine target substances. Preferably, by selection of the reagent gas, the method should be able to be optimized for certain target substances, or it should be possible to suppress interferents. The method should be able to be operated in the positive and negative mode if possible.

SUMMARY OF THE INVENTION

Our own unpublished investigations have proven that acetone can be substituted to certain limits by other proton affine substances, such as ether, particularly diethylether $C_2H_5OC_2H_5$ or also by ketones, esters, alcohols or amines.

The object of the present invention is solved in that the reagent gas molecules display a large cross section in the spectral range of the VUV radiation for the formation of positive molecular ions and a relatively small probability of the formation of protonated quasi-molecular ions.

In this way, ions are formed directly during irradiation instead of protonated quasi-molecular ions, whereby a sufficient concentration of reagent gas ions is formed and the ionization potentials, not the proton affinities, are crucial to the further ionization transfer to the target molecules.

Preferably, the ionization potential of the reagent gas molecules is equal to or less than the energy hv of the light quanta of the VUV radiation, however greater than the ionization potential of the sample molecules.

In this way, direct ionization capability of the reagent gas molecules is ensured by the VUV light and the direct charge transfer to the sample molecules.

In embodiments, the ionization potential of the reagent gas molecules is slightly smaller than hv, which guarantees a particularly effective ionization process by the VUV radiation.

In other embodiments, the ionization potential is however much smaller than hv. In this way, the detection of those interfering gas molecules with ionization potentials lying between hv and the ionization potential of the reagent gas molecules, is suppressed.

The method according to the invention is particularly advantageous when the sample gas molecules have a small absorption cross section on the spectral range of the VUV radiation, since in this case the direct ionization of the sample gas molecules practicably does not take place and amplification via the ionization of reagent gas molecules is quite considerable.

In a preferred embodiment, the ionization of the sample gas molecules is effected by a direct charge transfer between the positive reagent gas molecular ions and the sample gas molecules, whereby the latter become molecular ions which are detected by the ion mobility spectrometer.

By selection of the reagent gas, its ionization potential can be adapted to that of the target substance. If it is only insignificantly higher, for example, the required charge transfer takes place and furthermore the detection of interfering gases with a higher ionization energy is "quenched", i.e. they pass on their charge to the reagent gas molecules even if they were originally ionized by the VUV light.

Direct ionization of the reagent gas molecules with a large ionization cross section via the VUV light releases electrons, the number of which can considerably exceed the number of electrons emerging from metallic structures of the cell by photoeffect, so that the negative operating mode is also significantly amplified.

The electrons emitted during the ionization of reagent gas molecules form $O_2^-$ ions with the atmospheric oxygen which attach themselves to electronegative target substance molecules associatively or dissociatively, and allow or amplify in this manner the negative operating mode of the ion mobility spectrometers. In a negative operating mode of the ion mobility spectrometers, a charge transfer consequently takes place whereby electrons formed during the ionization of the reagent gas molecules first attach themselves to atmospheric air molecules and then are associatively or dissociatively collected by the more electronegative sample molecules, which become negative molecular ions that are detected by the ion mobility spectrometer.

In preferred embodiments, the reagent gas is a hydrocarbon, especially with double bonds, preferably an aromatic compound which has a greater ionization energy than the target substance and which is ionized in air under irradiation by the VUV lamp while releasing electrons but is nor, or only to a negligibly small extent, protonated.

In this way, hydrocarbon molecules are first positively ionized by the VUV light. Since they have a good ionization cross section and higher ionization potential than the target molecules, they pass on their charge to these directly. The process depends on the difference in the ionization potentials, not in the proton affinities.

The reagent gases benzene, toluene and xylene have proven themselves in tests to be particularly advantageous. They have good ionization cross sections, their ionization potentials are well adapted to the spectral ranges of current VUV lamps and to the potentials of target substances of interest in the military and nonmilitary fields, particularly also to those which have low proton affinities and they have also convincing amplifications of selectivity and sensitivity in the negative operating mode.

It is therefore particularly preferable if the reagent gas contains one of these three substances. In a preferred manner, the reagent gas is added to the sample gas and not, as in prior art, to the carrier gas of the spectrometer.

This has the advantage of greater variability. The spectrometer can easily be operated with or without reagent gas and also with various reagent gases. The presence of reagent gas in the carrier gas would mean a continuous load for the circulation filters. When changing the reagent gas, the hermetic circulation would have to be opened which also means a high load for the filters due to the infiltration of atmospheric humidity.

To carry out this method, a reagent gas R is admitted to the ionization compartment of the ion mobility spectrometers where it is ionized by the VUV light of the lamp. In this way positive ions $R^+$ and electrons $e^-$ result which become attached to atmospheric oxygen, i.e. negative ions of the type $(H_2O)_nO_2^-$ are formed. Both these ion types represent ionizing collision partners for the pollutant molecules to be detected. in positive polarity of the ion mobility spectrometers, ionization of the pollutant molecules M generally takes place in accordance with $M+hv \rightarrow M^+ + e^-$. However this reaction assumes that the molecule M can absorb the VUV light of the lamp. Should this however not be possible, or only slightly possible, if the molecule M does not possess the appropriate structure, ionization of the pollutant molecules M can also take place indirectly via collision with the reagent gas molecule ions $R^+$ in accordance with $R^++M \rightarrow R+M^+$. It is a prerequisite for this that the ionization potential of the pollutant molecule be less than or equal to that of the reagent gas molecule. The range of pollutants to be detected can be determined by the level of ionization potential of the reagent gas molecules: Those pollutants with ionization potentials between the light quantum energy hv and the potential of the reagent gas molecule, are ionized by the light, however they are neutralized again by the reagent gas molecules and therefore withdrawn from detection.

In negative polarity of the ion mobility spectrometers, two ways are possible for ionization of the pollutant molecules which are now abbreviated to (AB):

$(H_2O)_nO_2^-+(AB) \rightarrow (AB)O_2^-+nH_2O$ "associative"
$(H_2O)_nO_2^-+(AB) \rightarrow A+B+O_2^-+nH_2O$ "dissociative"

These reactions also occur when the ionization potential of the pollutant molecules is greater than the light quantum energy and/or when the pollutant molecules cannot directly or can barely absorb the light of the VUV lamp.

The method according to the invention can be combined with prior art methods, particularly the detection of proton affine target substances can take place as usual, e.g. with the addition of acetone, the detection of substances with reduced proton affinity and/or strong electronegativity, however, with the method according to this invention.

An ion mobility spectrometer which is designed to perform the method according to the invention, also falls within the scope of the invention.

Further advantages of the invention are evident from the description and the attached drawing. In addition, according to the invention, the above characteristics and the further characteristics described can be applied either individually or in any combination. The embodiments described are not to be understood as a complete list, but are rather of an exemplary nature.

BRIEF DESCRIPTION OF THE DRAWINGS

The invention is represented in drawings and is described and explained referring to specific embodiments.

DETAILED DESCRIPTION OF THE PREFERRED EMBODIMENTS

Figure 1:
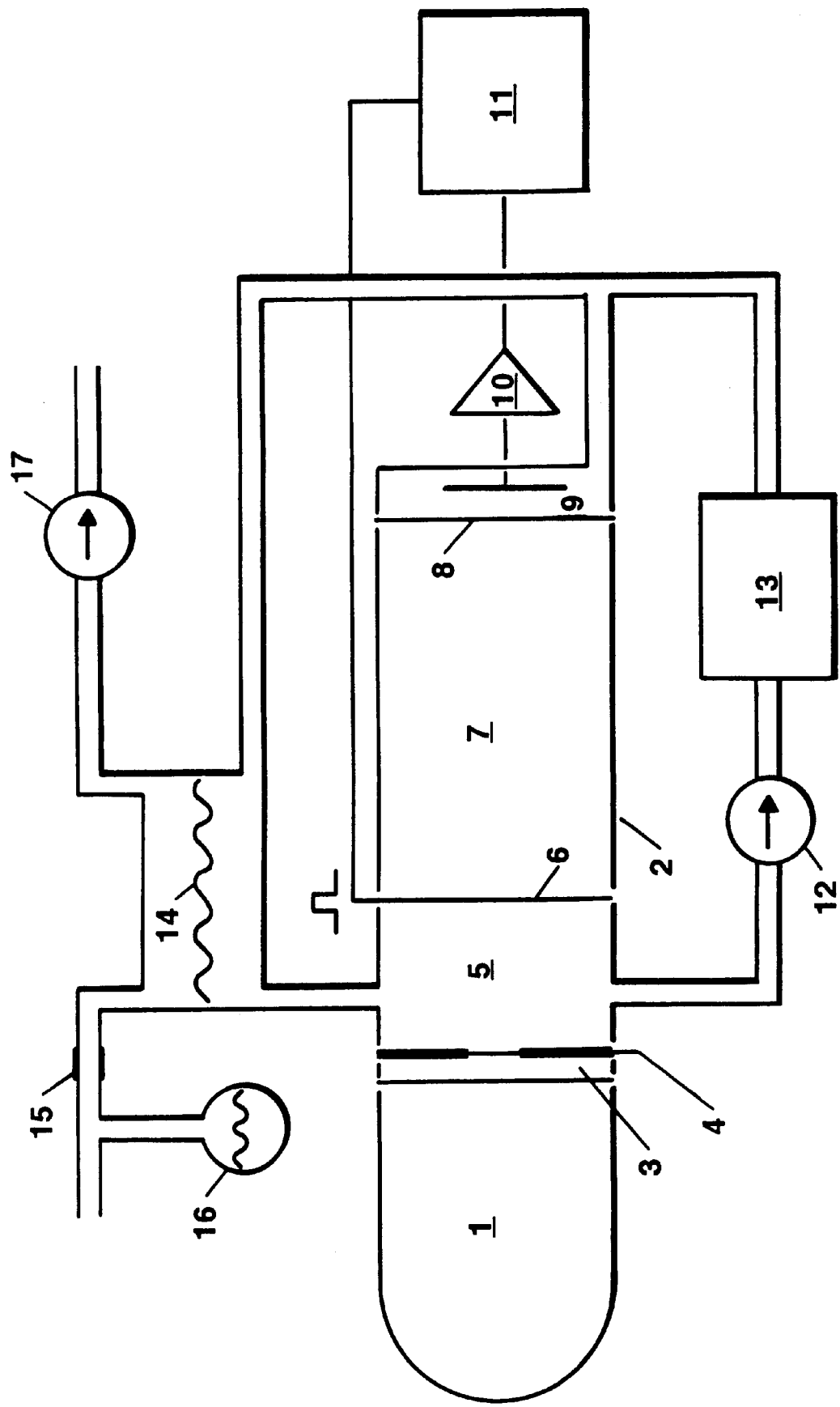
FIG. 1 A gas flow and circuit diagram of a photo-ionization ion mobility spectrometers for performance of the method in accordance with the invention.

FIG. 1 shows the schematic construction of an embodiment of a photo-ionization ion mobility spectrometer to perform the method according to the invention. The DC operated VUV lamp 1 is attached axially to the measuring cell 2 of the ion mobility spectrometers. Its effective spectral range is 10 to 10.6 eV. The UV light of lamp 1 passes through a VUV permeable window 3 made of magnesium fluoride, on which is located a high voltage electrode 4, into ionization chamber 5 of the measuring cell 2. At the axially opposite end of ionization chamber 5 is ion switch grid 6. Past this is drift chamber 7 which contains a control grid 8 and the ion detector electrode 9 at its axially far end. This electrode 9 is electrically connected with the input of a measurement amplifier 10. The amplifier signals enter micro-controller 11 and are digitized and processed there. At measuring cell 2, the circulation pump 12 and circulation filter 13 components are also located for the circulation of the carrier gas as well as the membrane inlet system 14 for the measurement gas. In front of the inlet system 14, the reagent gas metering unit 16 is placed in the area of the measurement air input 15, and the measurement air pump 17 is positioned after the inlet system 14.

Pump 17 draws the measurement air which contains the pollutant molecules to be detected, past the reagent gas metering unit 16, whereby the reagent gas or vapor is added to the measurement air, and then through the primary side of the membrane inlet system 14. Through the membrane of the inlet system 14, a portion of the pollutant and reactive gas molecules permeates into the secondary side of the inlet system 14. There they are captured by the carrier gas stream and transported into the ionization chamber 5 where they can be ionized by the VUV light from lamp 1. Pump 12 moves the air with the non-ionized molecules from measurement cell 2 and forces it through filter 13 where it is cleaned and dried. At the output of filter 13, the air stream divides into the drift gas stream which enters the drift chamber near electrode 9, and into the carrier gas stream which flushes out the secondary side of the membrane inlet system 14.

The positive pollutant and reagent gas ions formed in ionization chamber 5 are repulsed by the high voltage electrode 4 attached to the lamp window 3 in the direction of the ion switch grid 6. Normally this grid 6 is impermeable for the ion stream, however it is opened, for example, every 30 to 50 ms for 0.3 ms in order to admit a cloud of pollutant and reagent gas ions into the drift chamber 7. On the way through drift chamber 7 the ion cloud separates. The lighter and therefore faster ions reach electrode 9 earlier than the heavier ions. There the ions are neutralized and give off a pulse-type measurement signal in amplifier 10, the size of which corresponds to the number of ions and therefore to the concentration of the pollutants or reagent gas in the drawn measurement air. The time which an ion type requires to pass through drift chamber 7, i.e. the so called drift time, from which the characteristic "mobility" of the ion is calculated, is determined by micro-controller 11 which also controls the entire measurement procedure, especially the high voltage at the switch grid, the pumps etc. Apart from the addition of reagent gas on the primary side of the inlet system 14, the fundamental manner of operation of a photo-ionization ion mobility spectrometer is known from the prior art.

In FIGS. 2a–4, ion mobility spectrometers spectra are represented which were obtained with a photo-ionization ion mobility spectrometer of the type described in FIG. 1. The abscissa is the operating time or drift time axis and the ordinate the measurement current axis. The peaks correspond to the individual types of ions present in the measurement gas of differing mobility, which are formed in ionization chamber 5 and pass through the drift chamber at differing velocities. The numbers of the peaks correspond to the normalized mobilities of the ions in the dimension $cm^2/Vs$. The areas under these peaks are listed in absolute units top right of the spectral representation, whereby they are arranged so that the number nearest the top of the figure corresponds to the first peak seen from the left. The number to the left beside the list represents the area under the entire curve trace of the spectrum and characterizes the total ion current.

Figure 2A:
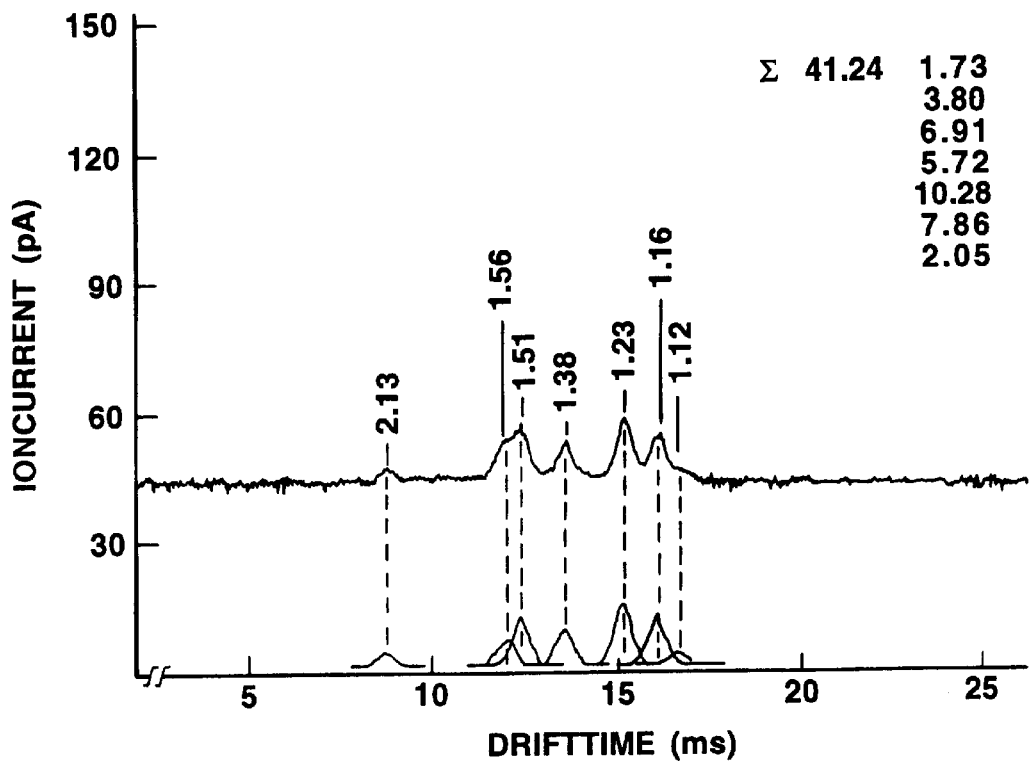
FIG. 2a Photo-ionization ion mobility spectrometers spectrum (positive operating mode) of 1.5 ppm of the skin chemical warfare agent sulfur-mustard gas in air without the addition of reagent gas.
Figure 2B:
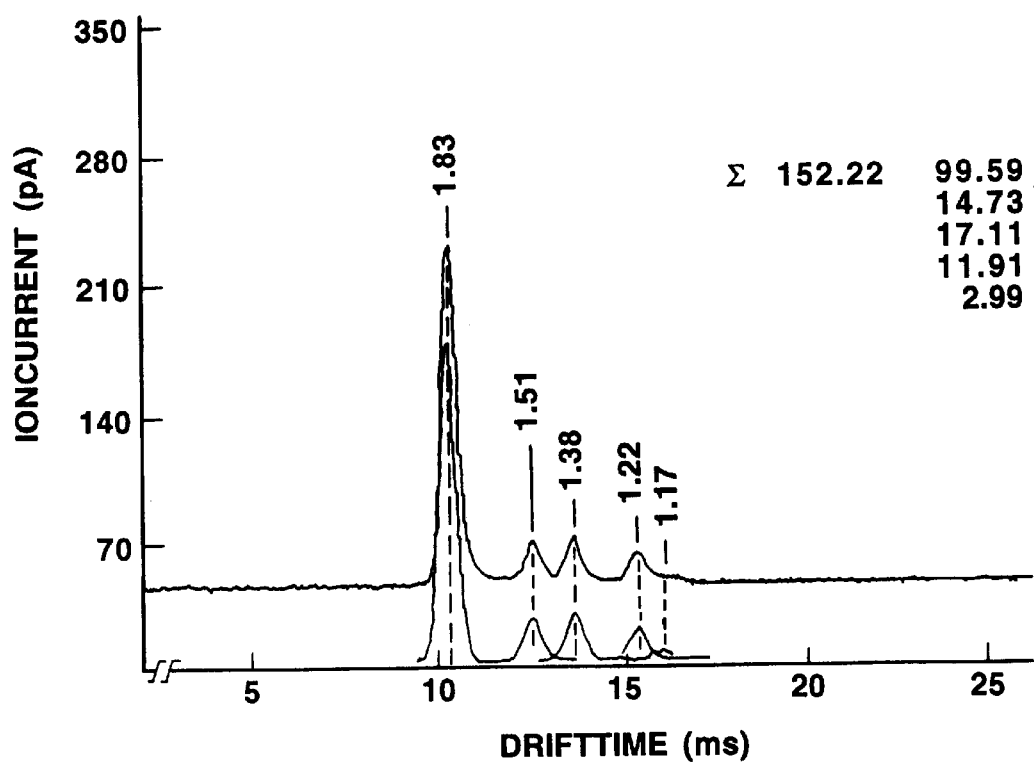
FIG. 2b Photo-ionization ion mobility spectrometers spectrum (positive operating mode) of 1.5 ppm of skin chemical warfare agent sulfur-mustard gas in air with the addition of approx. 250 ppm of the reagent gas acetone.
Figure 2C:
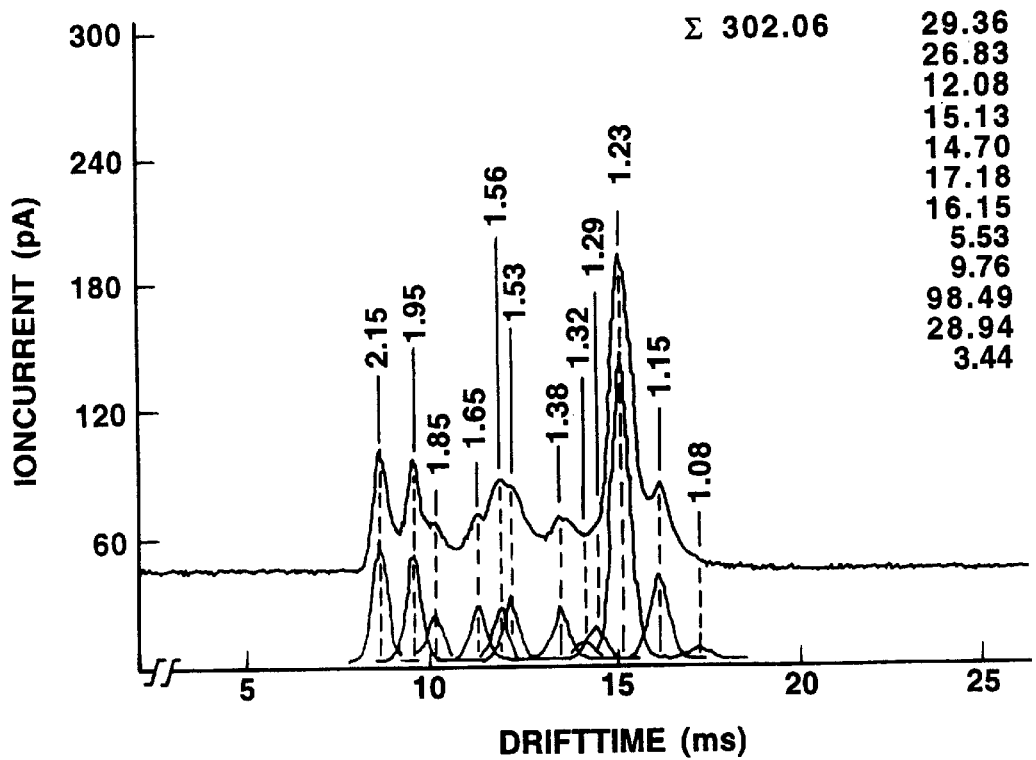
FIG. 2c Photo-ionization ion mobility spectrometers spectrum (positive operating mode) of 1.5 ppm of skin chemical warfare agent sulfur-mustard gas in air with the addition of 300 ppm of the reagent gas benzene.

Individually, FIGS. 2a to 2c show the spectra of the chemical sulfur-mustard gas (HD) in the positive operating mode of the ion mobility spectrometers. The chemical warfare agent (CWA) concentration amounts to 1.5 ppm respectively. In the sample, beside the active substance bis-(2-chloroethyl)-thioether, there are other completely characteristic chemical stabilizers and companion substances from the technical synthesis and hydrolysis products of the chemical warfare agent.

The spectrum in FIG. 2a was obtained without addition of reagent gas.

In FIG. 2b, the CWA-relevant trace amounts (the sum of areas of the peaks with normalized ion mobilities less than 1.7 $cm^2/Vs$) with the addition of approx. 250 ppm acetone as a measurement gas, remain almost unchanged in comparison to FIG. 2a. Only an additional very strong peak, caused by protonated acetone, appears at 1.83.

In FIG. 2c however, after mixing in approx. 300 ppm benzene vapor as measurement air, the chemical warfare agent-relevant signal contributions are about six times greater, whereby the detection of mustard gas at sublethal concentrations becomes possible with a photo-ionization ion mobility spectrometer.

The ineffectiveness of the acetone addition (FIG. 2b) is based on the fact that mustard gas has a proton affinity which is less than that of the reagent gas acetone, so that no ionization is possible by proton transfer and essentially the only effect that occurs is that a large acetone peak appears, however the characteristic peaks are not amplified.

On the other hand, the ionization cross section of benzene at 9.25 eV is quite large and the ionization energy from benzene is higher than that of mustard gas, so that a charge transfer from the benzene ions to the chemical warfare agent and partially also to the characteristic companion substances occurs, i.e. the benzene peak disappears in the spectrum again for the most part and the characteristic peaks are correspondingly amplified.

Figure 3A:
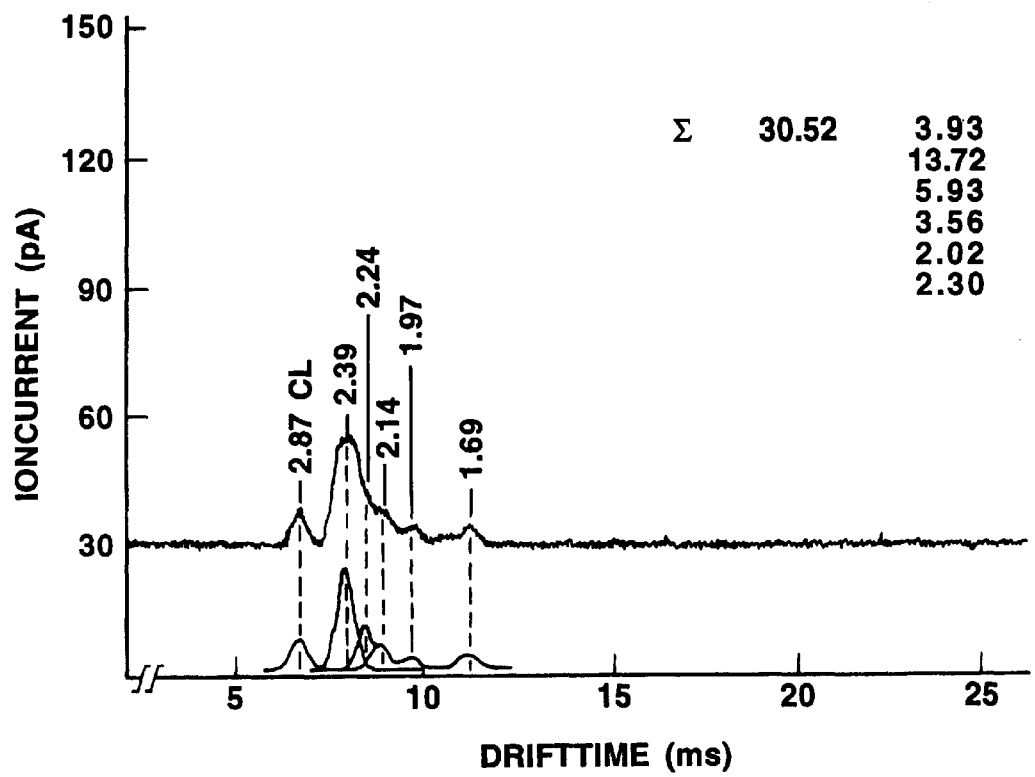
FIG. 3a Photo-ionization ion mobility spectrometers spectrum (negative operating mode) of 2 ppm chloropicrin ($Cl_3CNO_2$) in air without the addition of reagent gas.
Figure 3B:
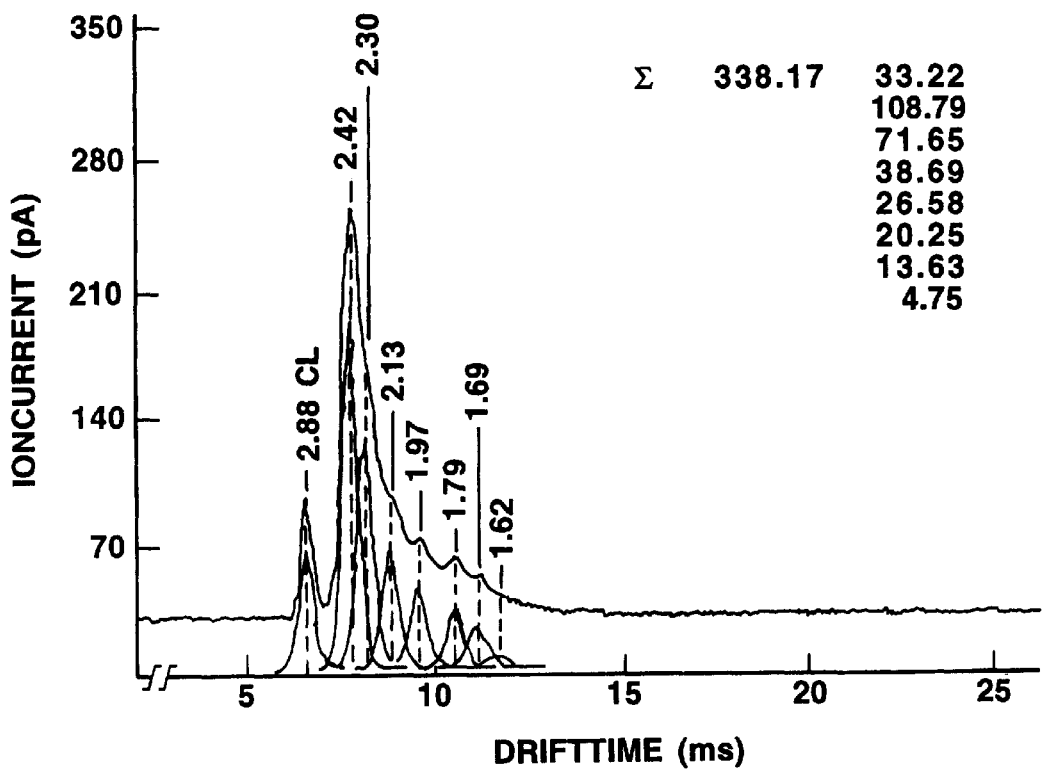
FIG. 3b Photo-ionization ion mobility spectrometers spectrum (negative operating mode) of 2 ppm chloropicrin (trichloronitromethane) in air with the addition of approx. 300 ppm of the reagent gas benzene.

In FIGS. 3a and 3b, the spectra for the lung chemical warfare agent nitrochloroform (trichloronitromethane) are represented. In the positive operating mode of the ion mobility spectrometers, no chemical warfare agent ions can be determined from this substance, not even after addition of a reagent gas such as acetone or benzene vapor. This is understandable since nitrochloroform is not proton affine, but rather strongly electronegative and possesses an ionization potential greater than 11 eV. Therefore it can neither be protonated nor directly or indirectly ionized via charge transfer from a reagent substance with a smaller ionization energy.

The detection of the chemical warfare agent is successful however in the negative operating mode of the ion mobility spectrometers. Through the high electron negativity of the chemical warfare agent molecule, a dissociative charge transfer occurs from the few negative ions of the measurement gas air to the chemical warfare agent molecules, whereby Cl ions form. This is visible in FIG. 3a, where approx. 2 ppm chloropicrin was measured in air without reagent gas. The negative ionization of the atmospheric oxygen hereby occurs primarily through photoelectrons from metal structures (switch grids) of the ionization cell 5, which is illuminated by the VUV light of the lamp.

In FIG. 3b, approx. 250 ppm benzene were mixed into the measurement gas. One recognizes a dramatic amplification of the characteristic spectrum with peaks at 2.43, 2.25 etc., which correspond to various water clusters of $O_2$ ions, including the chloride peaks at 2.88 $cm^2/Vs$. The addition and ionization of reagent gas molecules has generated more electrons which are available for the associative and dissociative ionization process of the pollutant molecules in the negative operating mode. In this case, the type of reagent gas is less significant. It is important that its molecules are ionized as well as possible by the VUV light, which Is primarily dependent upon the degree of light absorption and the ionization potential. It has been shown that in this case aromatic compounds, in particular benzene, toluene and xylene, are the most effective reagents, much better than acetone for example.

Figure 4:
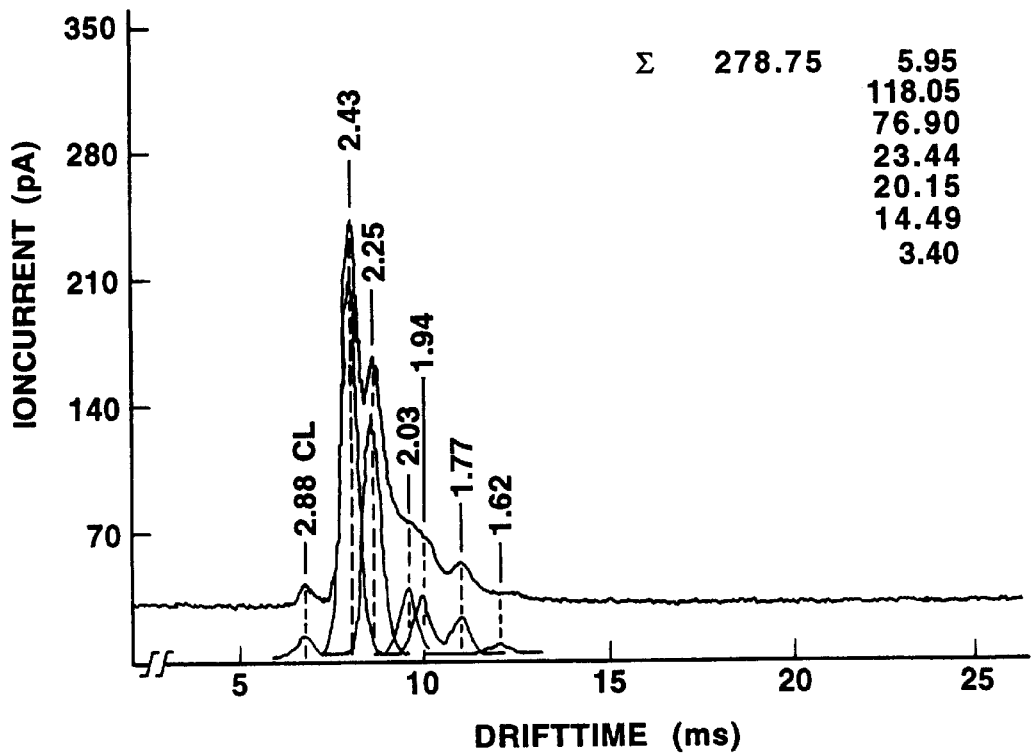
FIG. 4 Photo-ionization ion mobility spectrometers spectrum (negative operating mode) of 2 ppm chlorine in air with the addition of approx. 250 ppm of the reagent gas benzene.

The same ionization mechanism can also be exploited for the detection of chlorine. The $Cl_2$ molecules possess an ionization potential of 11.5 eV, and are consequently not capable of being ionized with the light quantum energies of 10–10.6 eV from standard VUV lamps. FIG. 4 shows the spectrum from 2 ppm chlorine after the addition of approx. 250 ppm benzene, scanned in the negative operating mode of the ion mobility spectrometers. The peak of the chloride ions resulting from dissociative charge transfer is clearly recognizable at 2.88 $cm^2/Vs$.

Figure 5:
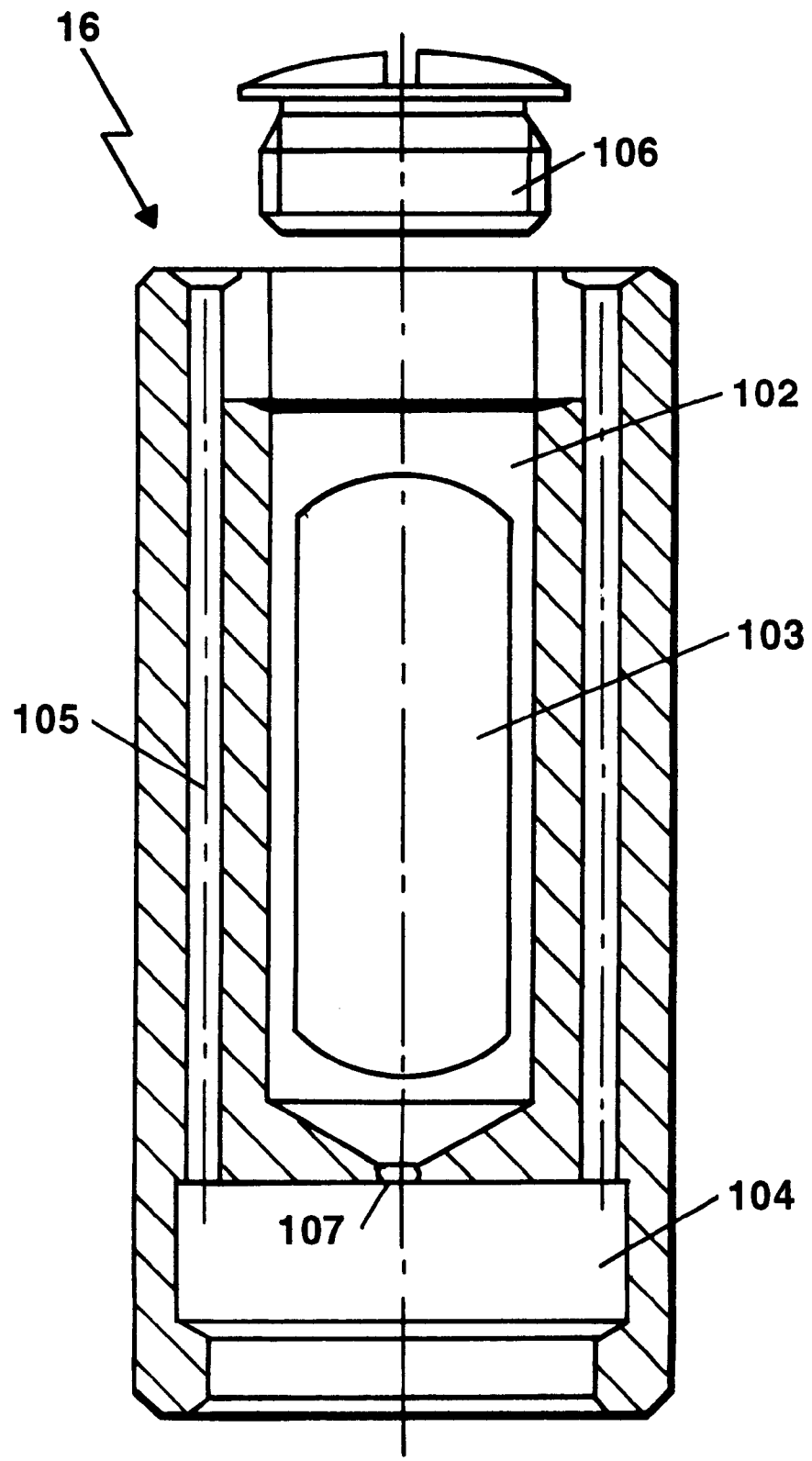
FIG. 5 Section through an injection device for reagent gases to the sample gas.

FIG. 5 shows in detail a section through a device 16 for the metering of reagent gases which represents a preferred embodiment of the metering device 16 schematically inferred in FIG. 1.

Device 16 is cylindrical and consists of a material which corresponds to the analytical requirements regarding absorption and dissorption of gas traces, e.g. of steel or high quality plastics. It has a first hollow chamber 102 for the reception of a reagent container 103, a second hollow chamber 104 for the mixture of reagent vapor with measurement air, and one or more canals 105 between the front end and the second hollow chamber 104.

The reagent selected for the operation of photo-ionization ion mobility spectrometers is enclosed in the reagent container 103, the walls of which are made of polymer material, or at least possess a window made of such material. Through this material, the reagent molecules permeate into hollow chamber 102. The one end of the hollow chamber 102 is sealed by the plug 106, at the other end is a passage in the form of a hole 107 to hollow chamber 104.

The measurement air which is drawn in by a pump (pump 17 in FIG. 1), streams through canal 105 into the hollow chamber 104 in which the reagent gas molecules also diffuse from hollow chamber 102 through hole 107, so that they mix with the measurement air in chamber 104. From there, the measurement air-reagent gas mixture passes into the primary side of the membrane inlet system (14 in FIGS. 1 and 6).

Figure 6:
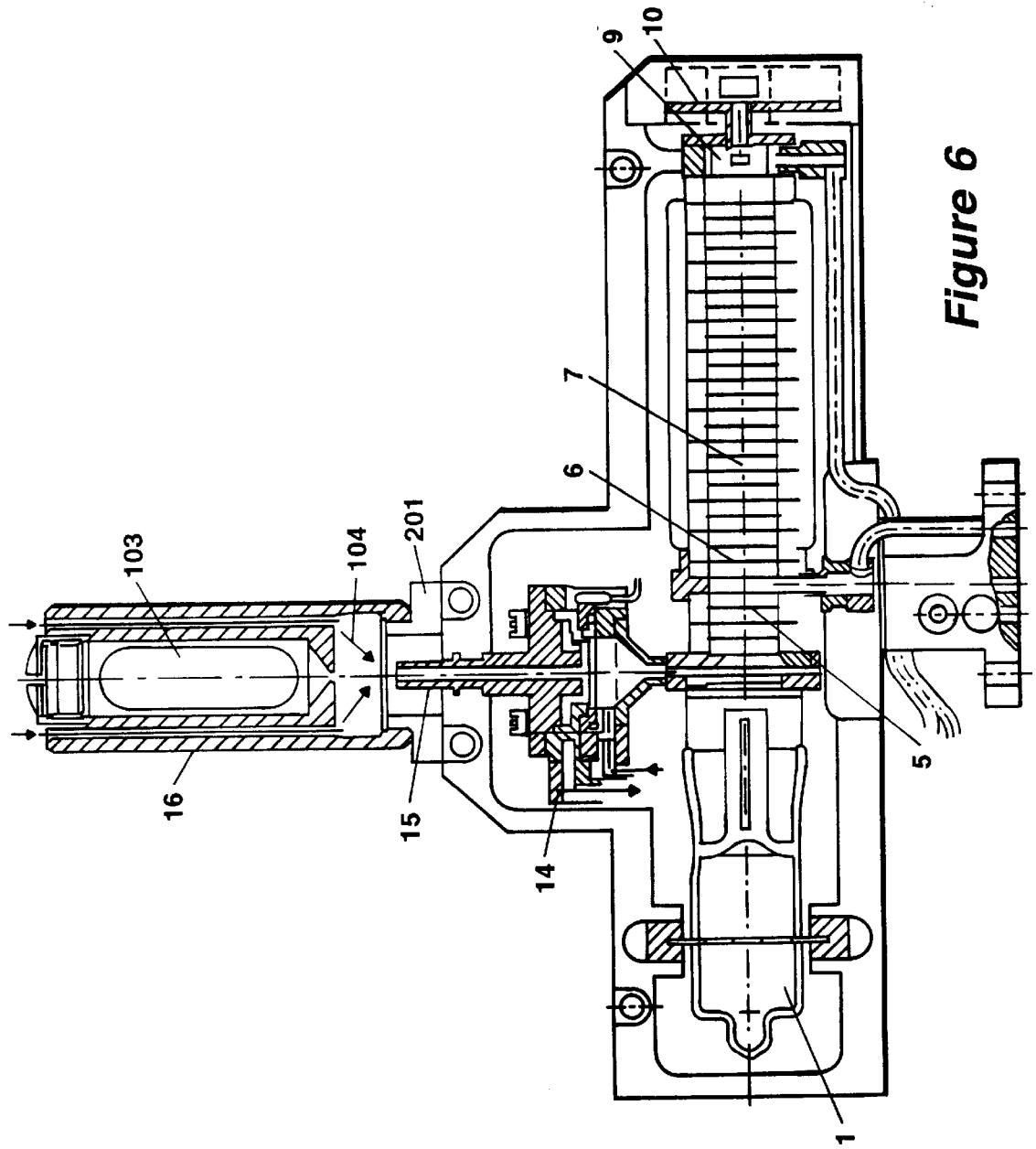
FIG. 6 Section through an embodiment example of a photo-ionization ion mobility spectrometers that is set up to perform the method according to the inventor.

FIG. 6 shows the arrangement of the metering device 16 at the measurement air input 15 of a photo-ionization ion mobility spectrometer. Identical and equally acting components of FIGS. 5 and 6 or 1 and 6 are marked with the same reference numbers. The output from hollow chamber 104 is connected via a sealing element 201 with the measurement air input 15. This connection is designed as easily removable, so that a quick exchange of the metering device 16 is possible by which the application range of the photo-ionization ion mobility spectrometers described here can be simply enlarged. The metering device 16 can be electrically heated.

It is understood that the characteristics mentioned in connection with FIGS. 5 and 6 are not limited to the design example, but rather can find use individually or in combination also with other embodiments of the invention.

We claim:

1. A method for the detection of gas traces in air by a photo-ionization ion mobility spectrometer, whereby a sample gas is fed into a photo-ionization chamber of the ion mobility spectrometer and sample molecules present in the sample gas are ionized by VUV radiation of a lamp and whereby this ionization is amplified by the addition of a reagent gas, wherein the reagent gas comprises at least one of benzene, toluene and xylene, and wherein the ionization potential of the reagent gas molecules is equal or less than the energy hv of the light quanta of the VUV radiation but greater than the ionization potential of the sample molecules.

2. The method of claim 1 wherein the sample gas molecules have an absorption cross section in the spectral range of the VUV radiation that is significantly smaller than that of the reagent molecules.

3. The method of claim 2, wherein the ionization of the sample gas molecules occurs in such a way that a charge transfer takes place between the positive reagent gas molecular ions and the sample gas molecules, whereby the latter become positive molecular ions which are detected by the ion mobility spectrometer in a positive operating mode.

4. The method of claim 3, wherein the addition of reagent gas occurs together with the sample gas.

5. The method of claim 1, wherein the addition of reagent gas occurs together with the sample gas.

6. A method for the detection of gas traces in air by a photo-ionization ion mobility spectrometer, whereby a sample gas is fed into a photo-ionization chamber of the ion mobility spectrometer and sample molecules present in the sample gas are ionized by VUV radiation of a lamp and whereby this ionization is amplified by the addition of a reagent gas, wherein the reagent gas comprises at least one of benzene, toluene and xylene, and wherein a charge transfer takes place whereby the electrons formed during the ionization of the reagent gas molecules first attach themselves to atmospheric oxygen molecules and then are associatively or dissociatively collected by more electronegative sample molecules, whereby the latter become negative molecular ions which are detected by the ion mobility spectrometer in a negative operating mode.

7. The method of claim 6, wherein the addition of reagent gas occurs together with the sample gas.

8. The method of claim 6, wherein the ionization potential of the sample molecules is greater than the energy hv of the light quanta of the VUV radiation.

9. The method of claim 8 wherein the addition of the reagent gas occurs together with the sample gas.

* * * * *